US005853663A

United States Patent [19]
Wittig et al.

[11] Patent Number: 5,853,663
[45] Date of Patent: Dec. 29, 1998

[54] PRESSURE DISTRIBUTOR AND MULTI-MACROCARRIER ASSEMBLY FOR BALLISTIC TRANSFER TRANSFECTION APPARATUS

[76] Inventors: Burghardt Wittig; Matthias Schroff; Joseph Schroff, all of c/o Shuguang Zhang, 25 Bowker St., Lexington, Mass. 02173-4142

[21] Appl. No.: 615,770

[22] Filed: Mar. 14, 1996

[30] Foreign Application Priority Data

Mar. 14, 1995 [DE] Germany .................. 195 10 696.2

[51] Int. Cl.⁶ .................. G01N 1/14; G01N 15/06; A61K 41/00; C07H 21/04
[52] U.S. Cl. .................. 422/50; 422/68; 435/285.3; 435/287; 435/52; 435/53; 514/44; 89/1.14; 536/24.3; 536/24.33; 536/23.1
[58] Field of Search .................. 514/44; 435/285.3, 435/172.1, 172.3, 287, 52, 53; 935/85; 89/1.14; 422/50, 68

[56] References Cited

U.S. PATENT DOCUMENTS 5,204,253  4/1993  Sanford et al. .................. 435/172.3
5,525,510  6/1996  McCabe et al. .................. 435/285.3

*Primary Examiner*—W. Gary Jones
*Assistant Examiner*—Dianne Rees

[57] ABSTRACT

The ballistic transfer transfection technology employs a cold gas shock wave to accelerate microprojectiles that carry matter into cells by mechanical force. The present invention relates to a device that splits the cold gas shock wave into several individual shock waves that spread the pressure of the initial shock wave to several projectile launching devices. The number of cells transfected by this new device is increased manyfold, compared to the original apparatus. The use of the technology in a clinical context is facilitated.

3 Claims, 6 Drawing Sheets a b

PRESSURE DISTRIBUTOR AND MULTI-MACROCARRIER ASSEMBLY FOR BALLISTIC TRANSFER TRANSFECTION APPARATUS

FIELD OF THE INVENTION

This invention relates to an improved part of an apparatus used to transfer matter into cells by accellerating particles in the direction of the cells. The particles deliver any matter adsorbed onto them upon passage through the cells.

BACKGROUND OF THE INVENTION

Many methods of modem cell biology require the transfer of matter, mainly nucleic acids, into living cells (hereafter referred to as transfection). Traditionally, this transfer of matter has been important to both the fields of biological and medical research. Recent progress, however, in the understanding of the body's functions as regarded to molecular mechanisms has led to the idea of treating human desease by using molecular approaches (colloquially referred to as "gene therapy"). Many of the biological methods suggested in this approach require the transfection of somatic cells. A number of techniques have been developed to achieve this aim: microinjection; electroporation; transfection by viral vectors or liposomes; and direct bombardment of cells with particles ("gene gun"). For a review on methods see *Methods in Enzymology* 217, (1993), pp. 461–655, (Academic Press, San Diego, Calif.).

Apart from microinjection, in which a single cell is injected directly with the transfecting matter, these methods suffer from a rather low and unreliable efficiency, efficiency being measured as percentage of successfully transfected cells out of total of treated cells. Microinjection's efficiency is very high; however, the number of treated cells is generally too low for this technique to be clinically valuable.

If the object of the transfection is to insert genetic information into the cell, then successful transfection requires the passage of the transfecting nucleic acid not only into the cell cytoplasm, but into the nucleus. The nuclear membrane is a barrier more difficult to cross than the cytoplasmic membrane. Many of the cells transfected by means of electroporation or lipofection that have incorporated the transfecting matter into their cytoplasm, will not express any genetic message transferred into them. For expression of any genetic message to happen, the genetic message has to pass into the nucleus. The transfection of cells with DNA by electroporation is most likely successful only when it happens during cell division, because the division process momentarily renders the nucleus permeable for the transfecting DNA.

In contrast, the ballistic transfection method achieves transport into the nucleus by the kinetic energy of the passing particle. The probability of nuclear passage of the microcarrier particle is governed by the ratio of nucleus diameter to cell diameter, which for many cells, is very favorable for nuclear passage. Thus, it can be expected that any clinical approach to transfection of cells with DNA would increase efficiency, employing the ballistic transfection method.

A current estimate of the number of transfected cells needed in a clinical protocol is in the order of $10^7$–$10^8$ cells. For the reasons given above, we believe that of the transfection methods mentioned, the ballistic transfer, i.e. directly bombarding cells with particles that carry the transfecting matter into the cells, has the greatest potential to achieve this aim.

Various embodiments of the idea of bombarding cells in order to achieve transfection have been published. They differ in the propulsion of the particles, the nature of the particles and various other aspects. A number of patents have been filed describing these embodiments (see: Jones, Frey, Gleason, Chee, Slightom: Gas Driven Microprojectile Accelerator and Method of Use U.S. Pat. No. 5,066,587; Jones, Frey, Gleason, Chee, Slightom: Gas Driven Microprojectile Accelerator WO 9111526, U.S. Pat. No. 471,216; Sanford, Wolf, Allen: Apparatus for Delivering Substances into Cells and Tissues in a Non-Lethal Manner EP 0 331 855; Tome: Improved Particle Gun EP 0 397 413; Brill, McCabe, Yang: Particle-Mediated Transformation of Animal Somatic Cells WO 91/00359; Mets: Aerosol Beam Injector WO 91/00915; WO 91/02071; Johnston, Williams, Sanford, McElligott: Particle-Mediated Transformation of Animal Tissue Cells WO 91/07487; Bruner, deVit, Johnston, Sanford: Improved Method and Apparatus for Introducing Biological Substances into Living Cells WO 91/18991; Bellhouse, Sarphie: Ballistic Apparatus WO 9204439, GB 9018892.1). However, only one embodiment to our knowledge, is commercially manufactured. This embodiment is the "Biolistic" apparatus invented by John C Sanford and manufactured under license from Cornell University and DuPont by Bio-Rad (Hercules, Calif.). The propulsion of the microcarriers is achieved in this embodiment by adsorbing the microcarriers to a macrocarrier polymer sheet, which is accelerated towards the cells by a cold gas shock wave. After retaining the macrocarrier, the microcarrier sheaf continues towards the target cell layer, eventually impacting and unloading the adsorbed transfecting matter into the cells.

The method of ballistic transfection implies that only a (sometimes large) fraction of the target cells is transfected successfully. The microcarrier sheaf is rarely homogeneous, and has to be of sufficiently small density in order not to kill too many of the target cells, which invariably suffer from stress exerted on them by both the shock wave and the impacting microprojectiles. A balance must be found between a high survival rate and a high transfection rate, which leaves part of the target cells untransfected. For a new and successful procedure to separate transfected cells from non-transfected cells, see our disclosure "Method to Separate Cells that have been Modified by Ballistic Transfer" (German application P 44 16 784.9).

As outlined above, the number of cells that need to be transfected in any clinical use of "gene therapy" will probably be in the order of $10^7$–$10^8$ cells, thus exceeding the efficiency of the "Biolistic" apparatus commonly in use today. It would constitute a great improvement to be able to increase tenfold the number of cells transfected in one shot.

Within the concept of the "Biolistic" system, only a limited range of improvements is feasible to achieve that aim. The number of cells reached by the impacting particles is equal to the product of area covered by the impacting microcarrier sheaf, by density of cells in that area.

The area of cells on the petri dish that is covered by the microcarrier sheaf depends on the distance between the macrocarrier stop and the dish. However, this distance can not be increased much, as a larger particle flight distance leads to a reduced kinetic energy of the particles at the time of impact.

The size of the macrocarrier sheet can not be increased much, as its mechanical properties are a consequence of its size.

The density of cells in a petri dish is at an optimum in a monolayer, as several layers are not well penetrated by the microcarriers, thus reducing transfection efficiency. In cell culture, not many cell types easily grow more than one cell layer in any case.

A possible solution is to increase the area covered in one operation of the apparatus by accelerating more than one macrocarrier, producing more than one microcarrier sheaf. The present invention refers to such an arrangement.

BRIEF DESCRIPTION OF THE DRAWINGS (All measures refer to millimeters, if not indicated otherwise)

Figure 1:
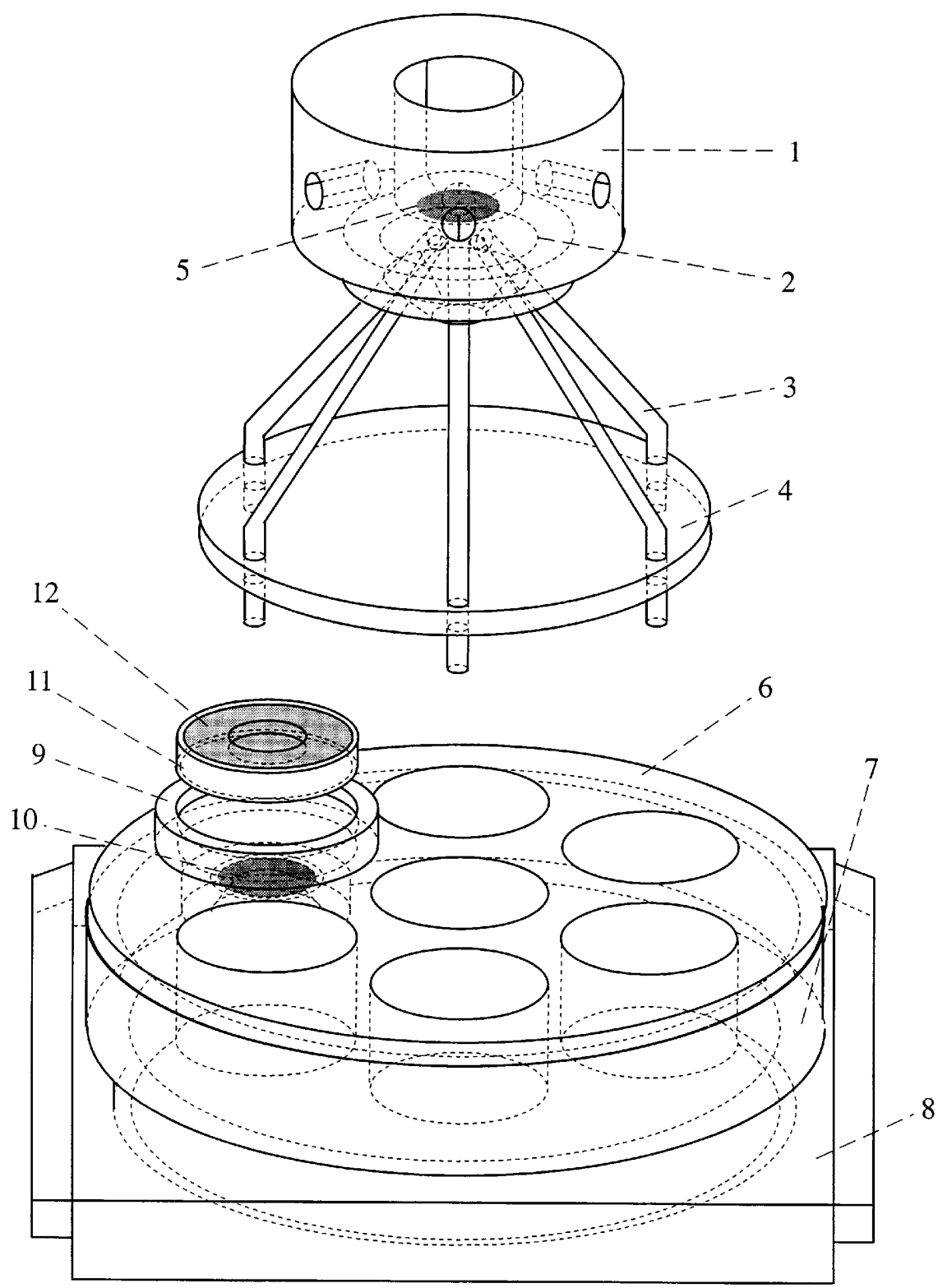
FIG. 1 shows a view of the assembled headpiece and plate. For clarity, only one macroprojectile launching device is shown.
Figure 2:
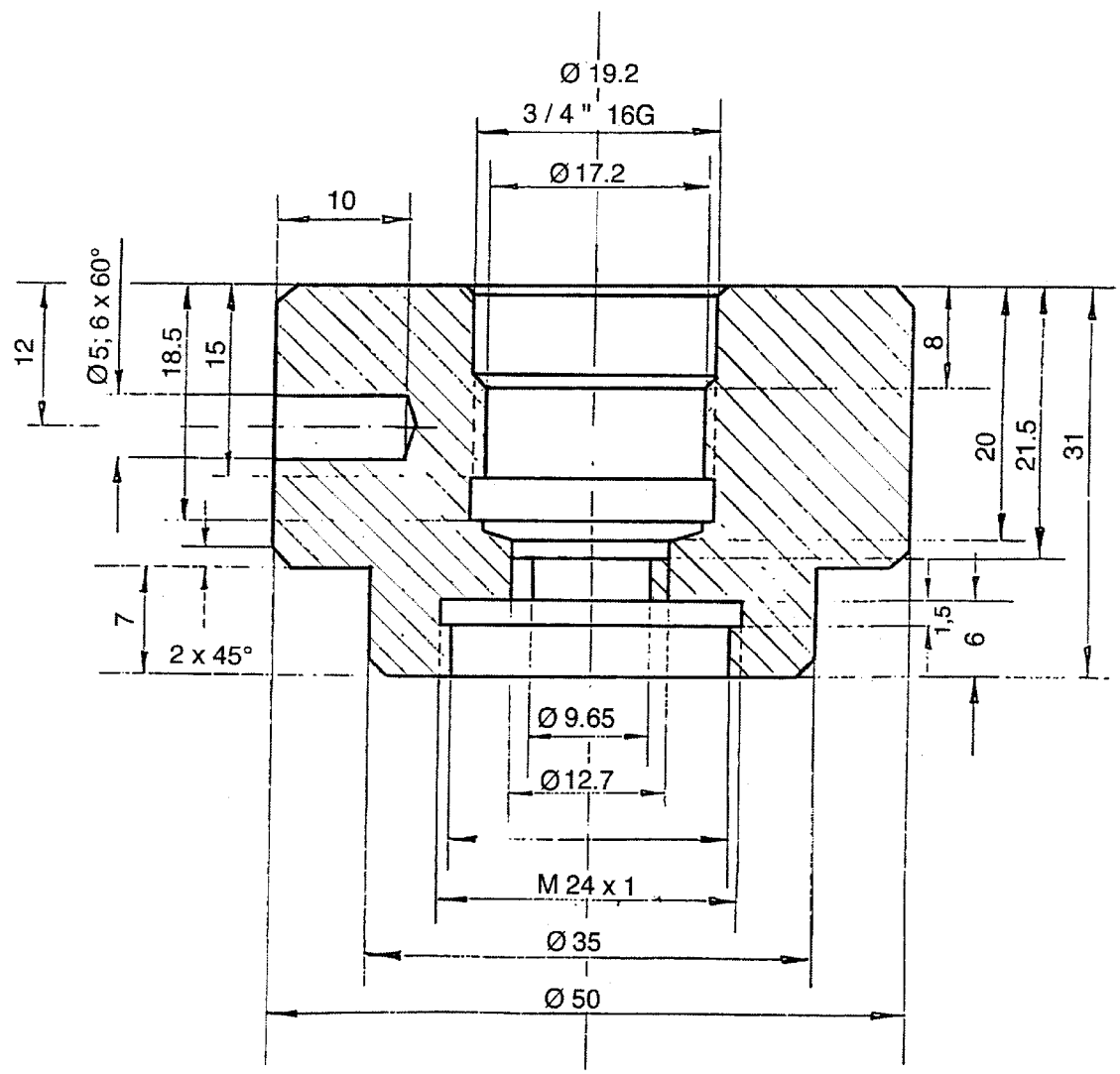
FIG. 2 shows a section of the flange.
Figure 3:
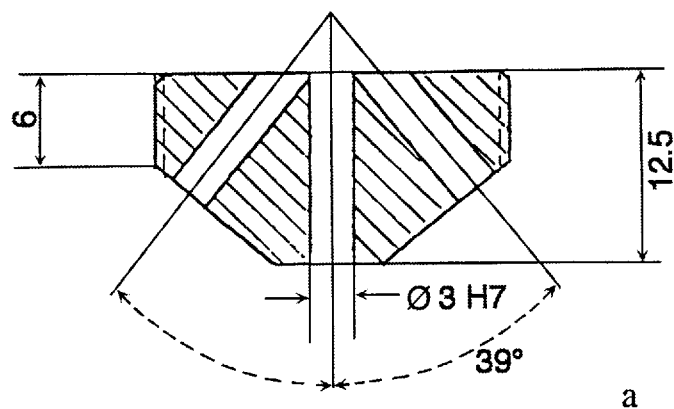
FIG. 3a shows a section, FIG. 3b a plan view of the pressure distributor.
Figure 3:
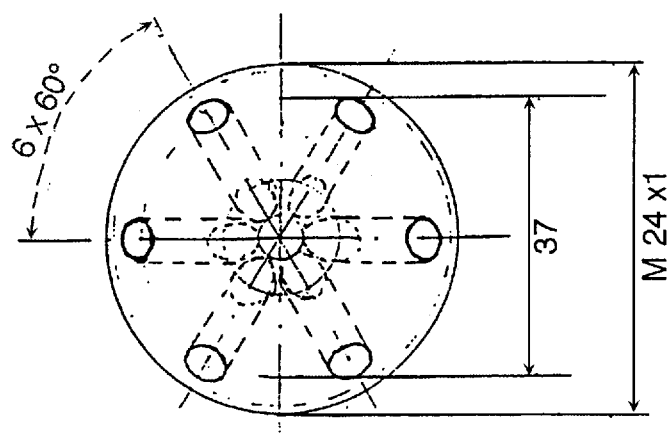
Figure 4:
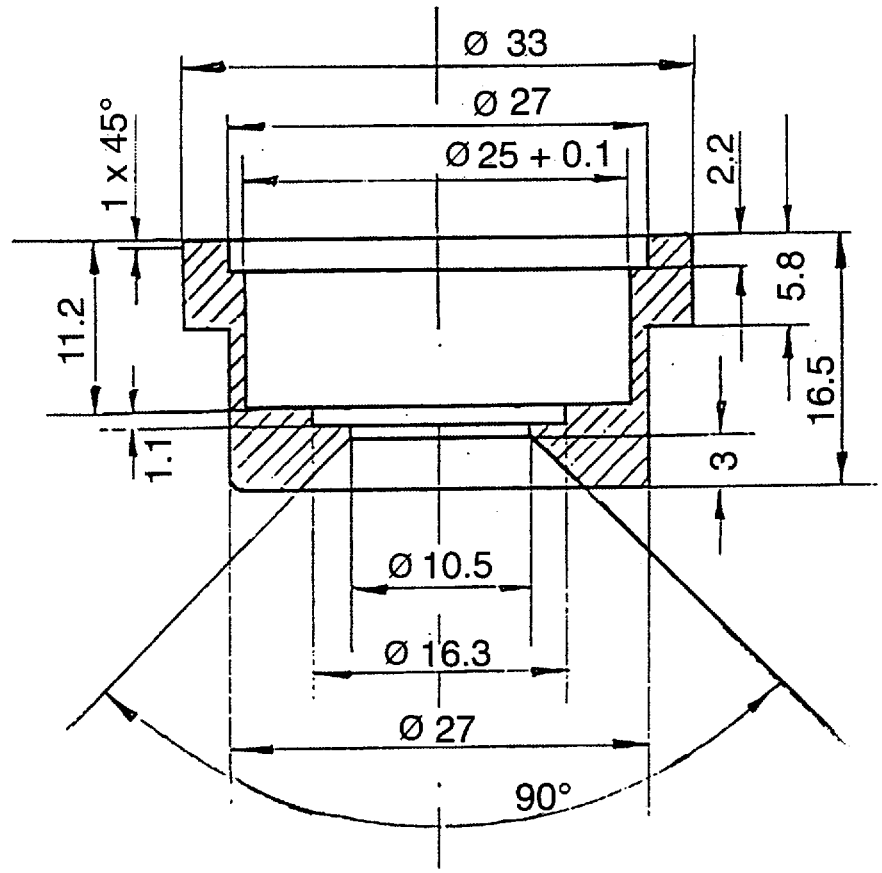
FIG. 4a shows a section of the insert that holds the retaining grid.
FIG. 4b shows a section of the ring plate in reverse orientation.
Figure 4:
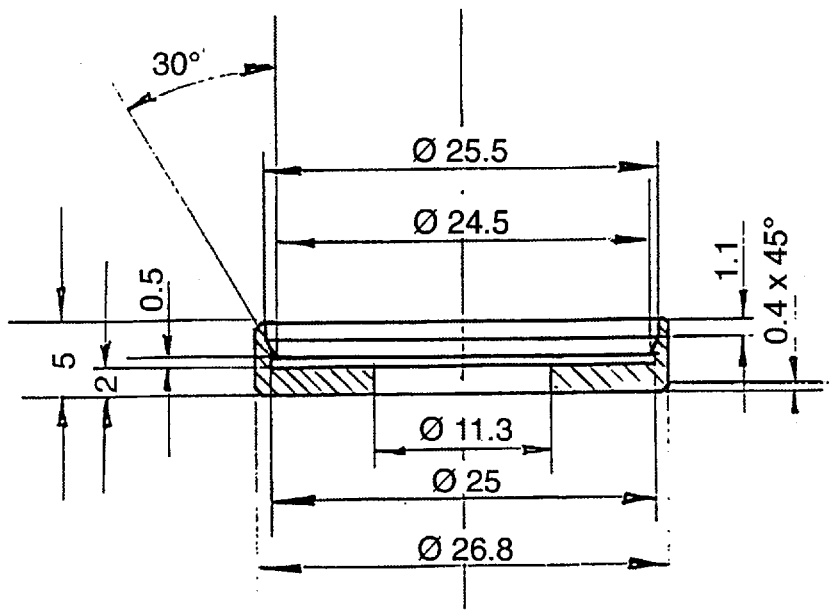
Figure 5:
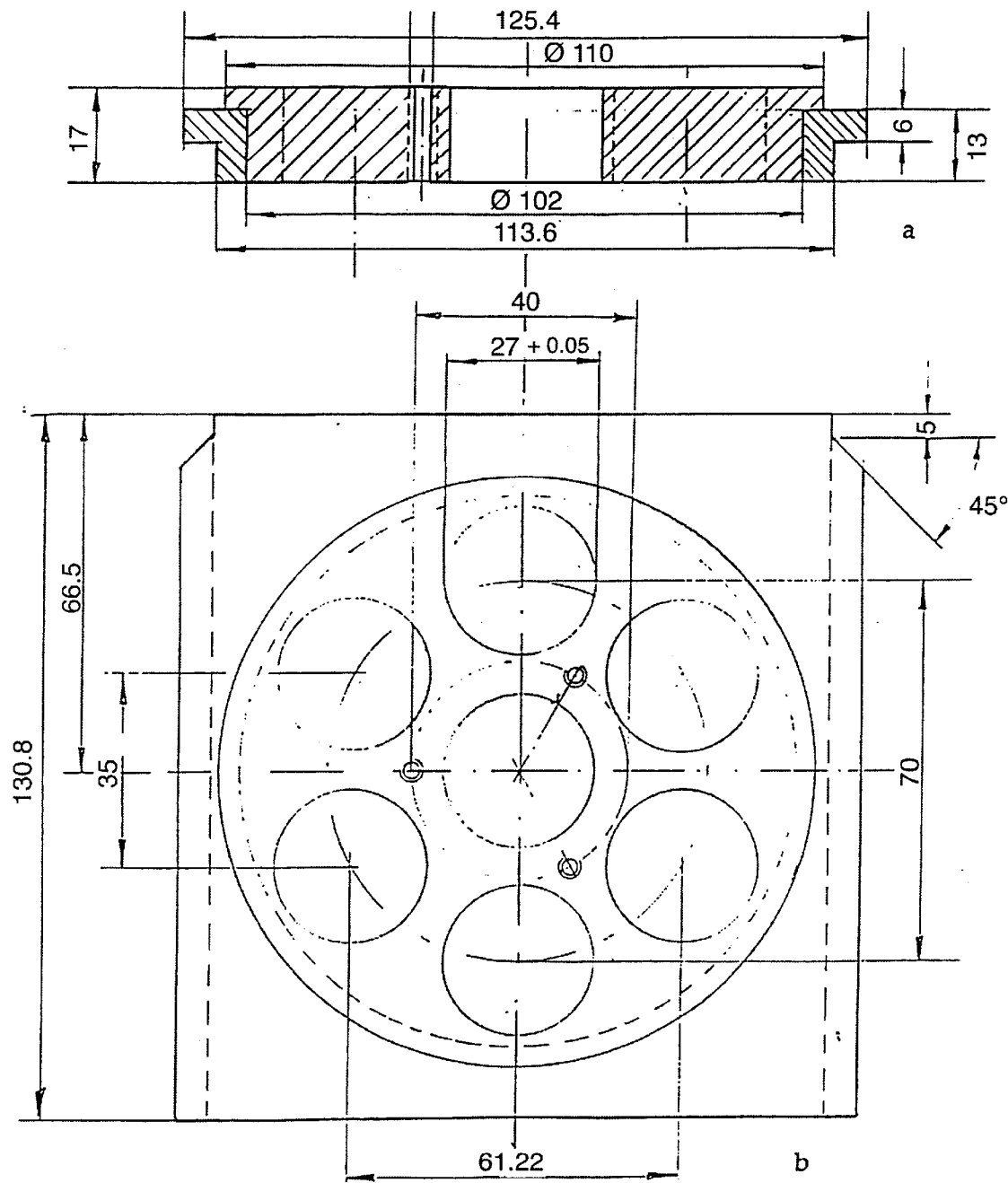

FIG. 5a shows a section of the inserting plate and the plate that receives the macroprojectile launching devices. The distance ring is not shown. FIG. 5b shows a plan view of the same pieces.

Figure 6:
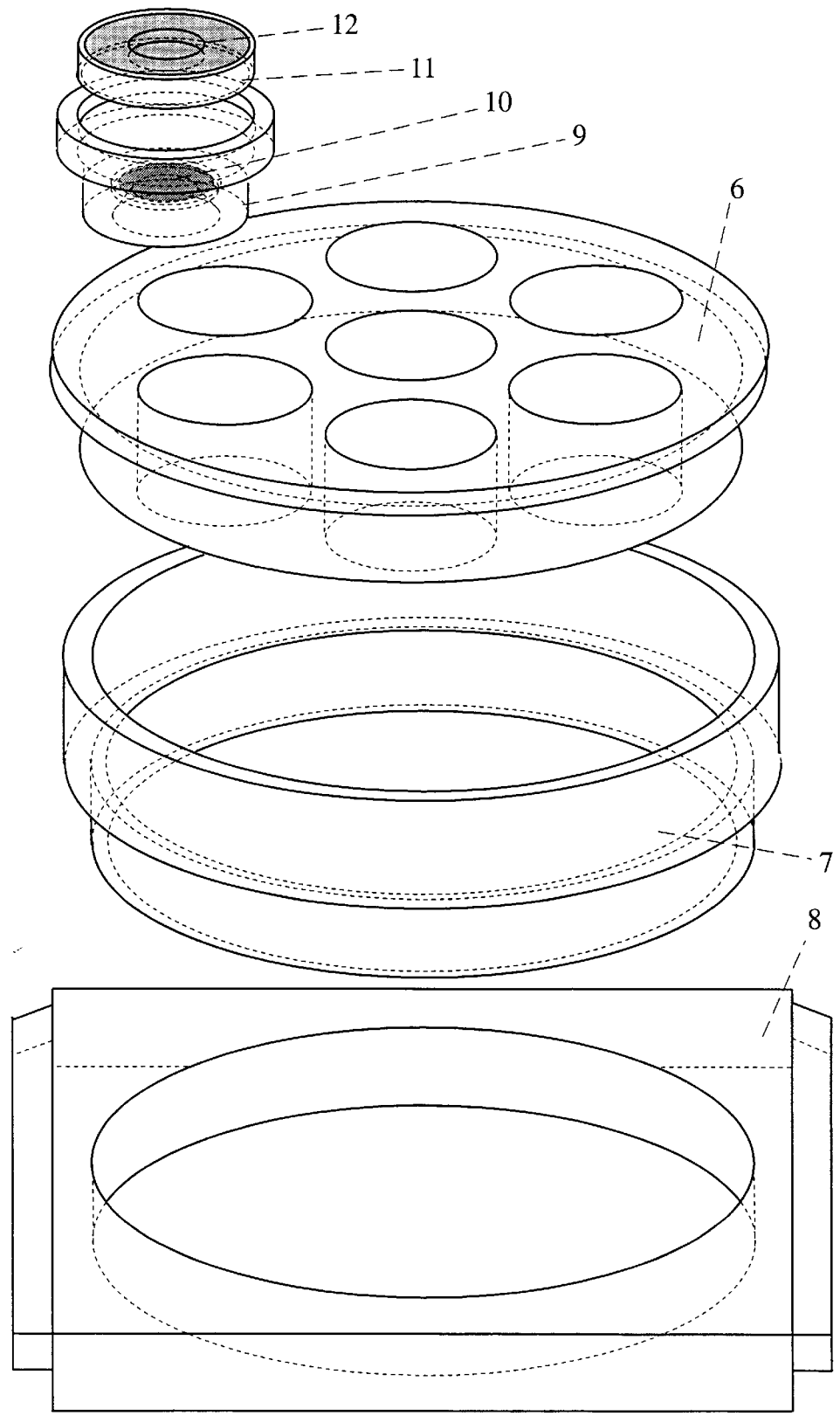

FIG. 6 is an exploded view of inserting plate, distance ring and receiving plate, and one macroprojectile launching device.

BRIEF SUMMARY OF THE INVENTION

The present disclosure relates to an improvement of the "Biolistic" apparatus that enables a plurality of macrocarriers, and the microcarriers adsorbed onto them, to be accelerated towards a number of cells that is increased compared to the existing apparatus.

According to the invention, the pressure entering the system and propulsing the macrocarrier is divided into several tubes. The tubes supply a plurality of macrocarrier launching devices with fractions of the original pressure burst, leading to a plurality of microprojectile sheafs impacting the target cells in an enlarged area. The device holding the rupture disc, dividing the pressure into several tubes supplying the macrocarrier launching devices (hereafter referred to as "headpiece"), as well as the plate holding the macrocarrier launching devices, said plate fitting into the slots provided by the original apparatus, are object of the present disclosure. The embodiment manufactured by us, consisting of a headpiece supplying seven macrocarrier launching devices, enabled us to transfect $1 \times 10^7$ cells (erythroleukemia cell line K 562) in one procedure, thus leading to a tenfold increase of cell number.

DETAILED DESCRIPTION OF THE INVENTION

According to one preferred embodiment, the headpiece consists of a flange 1 and a pressure distributor 2 with tubes 3 being fixed in their position by a plate 4. The headpiece is manufactured as a constructive unit and is not to be disassembled during the use of the device. All parts are made of stainless steel and connected to each other by industrial glue or welding. The flange 1 is equipped with a thread corresponding to the thread in the "Biolistic" apparatus manufactured by Bio-Rad, onto which it is screwed after insertion of the rupture disc 5.

The plate 6 that receives the macroprojectile launching devices is mounted onto the inserting plate 8 via the distance ring 7. Optionally, a thread between 7 and 8 can be used to adjust the relative vertical position of the macroprojectile launching devices, which facilitates an adjustment of the particle energy.

The plate 6 receives the inserts 9 that hold the grids 10 that retain the macroprojectiles. On this lies the ring plate 11, which receives the macroprojectile 12. The combination of insert 9 and ring plate 11 is referred to as microprojectile launching device.

EXAMPLE

The headpiece is screwed onto the "Biolistic PDS 100/He" apparatus manufactured by Bio-Rad®, Hercules, Calif. It is tightened with the torque supplied by the manufacturer. The inserting plate 8 is fit into the third groove from below. The plate receiving the macroprojectile launching devices is turned in order to place each of the launching devices directly under a tube ending. The plate that supports the petri dish is fit into the lowest groove.

A suspension of colloidal gold (30 μl, 1.6 μm diameter, 30 mg/ml, Bio-Rad®, Hercules, Calif.) is transferred onto each of seven macrocarrier polymer sheets (Bio-Rad). The gold is allowed to sediment, and the supernatant is removed. The gold is resuspended in a mixture of one part aqueous solution of DNA (fluorescein-endlabeled oligodesoxynucletides 50 μg/ml) and one part suspension of colloidal superparamagnetic particles (65 nm diameter, Miltenyi GmbH, Bergisch Gladbach, Germany, used as purchased). The suspension of superparamagnetic particles may be dialysed against PBS (phosphate buffered saline) in order to remove residual sodium azide added to the storage buffer. After sedimentation, the supernatant is removed and the residual gold is allowed to dry.

$1 \times 10^7$–$2 \times 10^7$ cells (erythroleukemia cell line K 562) in 10 ml RPMI medium (10% fetal calf serum) are transferred onto a 9.8 cm petri dish and dispersed evenly. The cells are left to incubate at a temperature of 37° C. overnight (5% $CO_2$). The following day, supernatant medium is removed, the cells are washed with ice-cold PBS, and all supernatant fluid is removed carefully. This is very important, as any liquid covering the cells decreases the transfection efficiency of the following transfection dramatically.

The ballistic transfer is conducted according to the operating protocol supplied by the manufacturer of the employed apparatus (Biolistic PDS 1000/He, Bio-Rad). The rupture disc ruptures at 1550 psi. The pressure of the lower vacuum chamber is 508 mm (20 inches) Hg.

The cells are resuspended after transfection in 1 ml ice cold PBS/BSA medium (5 mM EDTA) and separated according to their magnetic susceptibility, as described in our patent application "Method to separate cells that have been modified by ballistic transfer"(U.S. application Ser. No. 08/435,388; filing date May 5, 1995; European Publication No. 0686 697 A2, filing date May 8th, 1995):

The separation procedure is conducted on a MACS-separation column (Miltenyi GmbH) according to the operating protocoll of the manufacturer. The entire process is conducted at a temperature of 4° C.: The cells are resuspended after transfection in 3 ml ice cold PBS/BSA medium (5 mM EDTA) and washed onto the column while in a magnetic field. The petri dish is washed again with 2 ml PBS/BSA, which is added to the column. The column is washed with three volumes of PBS/BSA medium (5 mM EDTA) at a flow rate of 0.3 ml/min. The fluid is retained and labeled N (non-magnetic). The magnetic field is removed and the column is flushed with one volume PBS/BSA medium (5 mM EDTA) in reverse direction to whirl up the retained cells. The magnetic field is applied again and the fluid is drained. The column is washed with four to five volumina of PBS/BSA medium (5 mM EDTA) at a flow rate of 0.6 m/min.

The magnetic field is removed and the retained cells are washed from the column by flushing with 3 ml of PBS/BSA medium (5 mM EDTA) in short pulses. The collected fraction is labeled M (magnetic). The collected fractions are subsequently assayed for their fluorescence in a flow cytometry scanner (FACS) (Becton Dickinson, Heidelberg, Germany).

What is claimed is:

1. An apparatus for the transfection of cells comprising:

a) a pressure separation means that divides a cold gas shock wave into more than one pressure wave that propel macroprojectiles into the direction of cells that are to be transfected by biological matter, b) a plurality of microprojectile launching devices and c) a macroprojectile launching device holding means positioned underneath said pressure separation means, holding in place said plurality of macroprojectile launching devices so as to expose said launching devices to the individual pressure bursts released by said pressure separation means.

2. An apparatus according to claim 1, where the pressure separation means diverts the cold gas shock wave into seven tubes generating a partitioned cold gas shock wave wherein said seven tubes comprise one central tube and six tubes arranged hexagonally around said central tube, each tube connecting to one of seven macroprojectile launching devices arranged in the same pattern as said seven tubes and wherein said seven tubes are suspended directly underneath the pressure separation means in a way which aligns each trajectory of the partitioned cold gas shock wave with each one of said macroprojectile launching devices.

3. An apparatus according to claim 2, wherein a pressure reducing means is built into one or more of the tubes to adjust the pressure exiting through said one or more tubes.

* * * * *